United States Patent
Hayashi et al.

(10) Patent No.: US 6,884,759 B2
(45) Date of Patent: Apr. 26, 2005

(54) PLANT-ACTIVATING AGENT

(75) Inventors: Toshio Hayashi, Wakayama (JP); Takayuki Nomura, Wakayama (JP); Tadayuki Suzuki, Wakayama (JP)

(73) Assignee: Kao Corporation, Tokyo (JP)

( * ) Notice: Subject to any disclaimer, the term of this patent is extended or adjusted under 35 U.S.C. 154(b) by 13 days.

(21) Appl. No.: 10/411,101

(22) Filed: Apr. 11, 2003

(65) Prior Publication Data

US 2003/0216261 A1 Nov. 20, 2003

(30) Foreign Application Priority Data

Apr. 11, 2002 (JP) ........................................ 2002-109257

(51) Int. Cl.$^7$ .............................................. A01N 31/02
(52) U.S. Cl. ....................................... 504/353; 503/354
(58) Field of Search .................................. 504/353, 354

(56) References Cited

FOREIGN PATENT DOCUMENTS

| EP | 0 998 850 A1 | 5/2000 |
|---|---|---|
| JP | 9-322647 A | 12/1997 |
| JP | 2000-198703 A | 7/2000 |

*Primary Examiner*—S. Mark Clardy
(74) *Attorney, Agent, or Firm*—Birch, Stewart, Kolasch & Birch, LLP

(57) ABSTRACT

This invention provides a plant-activating agent which can activate plants effectively and give a liquid preparation stable in storage for a long time. In this invention, (A) a $C_{12-19}$ mono-alcohol and (B) a $C_{20-30}$ mono-alcohol are used together with a surfactant, a fertilizer component and a chelating agent if necessary.

11 Claims, No Drawings

PLANT-ACTIVATING AGENT

TECHNICAL FIELD

This invention relates to a plant-activating agent and a method of activating a plant by applying the same in a solution or solid form onto roots, stems, leaves or fruits in a method of spraying onto leaves or irrigating into soil. Hereinafter, the "plant" refers to plants recognized from the term plant itself or to plants such as vegetables, fruits, fruit trees, cereals, seeds, bulbs, flowering plants and herbs, as well as plants in taxonomy.

PRIOR ARTS

To increase the yield by promoting the growth of agricultural products and increasing the crop per unit area is an important problem for agricultural production, and for the purpose of improvements in productivity etc., fertilizers containing nutrient elements essential for plant growth have been used.

The fertilizer is supplied to plants by giving it as initial or additional fertilizer or by spraying its solution onto leaves or irrigating it into soil, but even if the fertilizer is given at a higher concentration than a predetermined level, the growth of plants and the crop are not so improved. On the contrary, if the fertilizer is supplied in excess, the balance among nutrients in soil may be lost or stress may be given to plants, so the growth of plants may be adversely affected.

Accordingly, a wide variety of plant growth regulators are utilized in addition to the fertilizer. For example, plant growth regulators represented by gibberellin and auxin have been used for regulating growth in germination, rooting, elongation, flowering and fruiting and for regulating morphogenesis reaction, but the action of these substances is diverse and complex, and their use is limited.

To solve these problems, techniques wherein a leave spray comprising oligosaccharides (JP-A 9-322647) or a liquid fertilizer containing sugars, minerals, amino acids, seaweed extracts and microbial fermentation extracts is sprayed onto leaves or given in a solution form are known, but at present these techniques cannot be said to be practically satisfactory in the effect.

Further, JP-A 2000-198703 discloses a plant-activating agent comprising a $C_{12-24}$ mono-alcohol, and describes that this agent can activate plants effectively without chemical damage.

When a plant-activating agent such as that described in JP-A 2000-198703 is used, it is preferable for operativeness that the plant-activating agent is in a liquid form such as an aqueous solution or an aqueous dispersion in advance, but from such $C_{12-24}$ mono-alcohol, a stable liquid preparation is hardly obtained in some cases. In particular, a liquid preparation stable in storage at high temperatures for a long time is hardly obtained.

DISCLOSURE OF INVENTION

The object of this invention is to provide a plant-activating agent which can activate a plant effectively and give a liquid preparation stable in storage for a long time.

This invention relates to a plant-activating agent composition comprising (A) a $C_{12-19}$ mono-alcohol and (B) a $C_{20-30}$ mono-alcohol. The composition may further comprise (C) at least one selected from the group consisting of a surfactant, a fertilizer component and a chelating agent.

Further, this invention relates to a plant-activating agent composition comprising particles having an average particle diameter of 0.01 to 500 μm comprising at least one selected from (A) a $C_{12-19}$ mono-alcohol and (B) a $C_{20-30}$ mono-alcohol. The composition may further comprises (C) at least one selected from the group consisting of a surfactant, a fertilizer component and a chelating agent.

In the composition of this invention, the ratio of (A)/(B) by weight is preferably 20/1 to 1/20. The composition may also comprise a thickener.

Further, this invention encompasses a plant-activating agent composition comprising (A) a $C_{12-19}$ mono-alcohol, (B) a $C_{20-30}$ mono-alcohol and (C') a nonionic surfactant and at least one selected from the group consisting of a fertilizer component and a chelating agent.

In addition, this invention relates to a method of activating a plant, which comprises supplying the composition described above to a plant.

DETAILED DESCRIPTION OF THE INVENTION

<Component (A)>

In this invention, a mono-alcohol containing 12 to 19 carbon atoms, preferably 14 to 19 carbon atoms, particularly preferably 16 to 19 carbon atoms is used as the component (A) because it can activate a plant effectively without chemical damage. The hydrocarbon group in the component (A) may be saturated or unsaturated, or linear, branched or cyclic. The hydrocarbon group is preferably linear or branched, particularly preferably a linear alkyl group. Examples of the mono-alcohol include lauryl alcohol, cetyl alcohol, stearyl alcohol and oleyl alcohol, alcohols derived from natural fats and oils, etc.

<Component (B)>

In this invention, a mono-alcohol containing 20 to 30 carbon atoms, preferably 20 to 26 carbon atoms, more preferably 20 to 24 carbon atoms is used as the component (B) in order to disperse the component (A) stably in water. The hydrocarbon group in the component (B) may also be saturated or unsaturated, or linear, branched or cyclic. This hydrocarbon group is preferably linear or branched, particularly preferably a linear alkyl group. Examples of the component (B) include eicosanol, behenyl alcohol and phytol, alcohols derived from natural fats and oils, etc. The difference in the number of carbon atoms between the components (A) and (B) is preferably 1 to 15, more preferably 1 to 10, particularly preferably 2 to 6, from the viewpoint of storage stability.

<Plant-activating Agent>

The plant-activating agent of the invention comprising the components (A) and (B) described above may be in the form of a liquid, a flowable agent, a paste, a hydrate, granules, powders, tablets, etc., but a liquid preparation (liquid) containing water is preferable. The granules, powders and tablets are stable when used in a liquid form. When water is contained in the plant-activating agent, its content in the plant-activating agent is preferably 30 to 99.9 weight-%, more preferably 50 to 99.9 weight-%, still more preferably 70 to 99.9 weight-%, from the viewpoint of storage stability. If necessary, an organic solvent other than water can be contained therein. Particularly in the case of the liquid preparation, a surfactant described later is simultaneously used from the viewpoint of improving storage stability.

The plant-activating agent of this invention in any forms described above preferably comprises particles having an average particle diameter of 0.01 to 500 μm comprising at least one of the components (A) and (B). More preferably, the plant-activating agent comprises particles having an average particle diameter of 0.01 to 500 μm comprising both the components (A) and (B). In the case of the liquid preparation, the average particle diameter of the particles is preferably 0.01 to 100 µm, more preferably 0.01 to 50 µm. In the case of solid preparations such as granules and powders, the average particle diameter of their particles is preferably 1 to 500 µm, more preferably 10 to 500 µm, still more preferably 30 to 300 µm. It is preferable for stability that the liquid preparation in particular comprises particles having these particle diameters. The presence of such particles can be confirmed by a laser diffraction/scattering particle size distribution-measuring meter, for example LA-700 manufactured by Horiba, Ltd.

In this invention, the liquid preparation attains excellent storage stability probably as a result of inhibition of growth of crystals of the components (A) and (B) by mixing the component (A) with the component (B).

When used, the plant-activating agent of this invention is sprayed onto leaves or roots of a plant, usually as an aqueous solution, an aqueous dispersion or an emulsion of the components (A) and (B) at a total concentration of 1 to 500 ppm (ratio by weight).

In the plant-activating agent of this invention, the ratio by weight of the component (A) to the component (B), that is, (A)/(B), is preferably 20/1 to 1/20, more preferably 10/1 to 1/10, still more preferably 5/1 to 1/1, from the viewpoint of achieving a stable liquid preparation.

In the method of supplying the plant-activating agent of this invention to a plant, various methods can be used. Examples of the methods include, a method of directly giving the powders or granules in an analogous manner to fertilizers, a method of spraying a diluted, aqueous solution thereof directly onto leaves, stems or fruits of plants, or injecting it directly into soil, or a method of supplying the plant-activating agent by diluting and mixing it with hydroponic water or supplied water in contact with roots during hydroponic culture or in rock wool.

The plants which can be treated with the plant-activating agent of this invention include fruits and vegetables such as cucumber, pumpkin, watermelon, melon, tomato, eggplant, green pepper, strawberry, okra, string bean, broad bean, pea, green soybean or corn; leaf vegetables such as Chinese cabbage, greens to be pickled, pakchoi, cabbage, cauliflower, broccoli, Brussels sprouts, onion, Welsh onion, garlic, shallot, leek, asparagus, lettuce, leaf lettuce, celery, spinach, garland chrysanthemum, parsley, wild chervil, Japanese parsley, udo, Japanese ginger, butterbur or beefsteak plant; and root vegetables such as radish, turnip, burdock, carrot, potato, taro, sweet potato, yam, ginger or lotus root. In addition, the plant-activating agent can also be used for rice plants, wheat plants, flowering plants etc.

For the purpose of emulsification, dispersion, solubilization or promoting permeation of the mono-alcohol, a surfactant described below is used preferably together with the components (A) and (B) in this invention.

Examples of nonionic surfactants include sorbitan fatty esters, polyoxyalkylene sorbitan fatty acid esters, polyoxyalkylene fatty acid esters, glycerin fatty acid esters, polyoxyalkylene glycerin fatty acid esters, polyglycerin fatty acid esters, polyoxyalkylene polyglycerin fatty acid esters, sucrose fatty acid esters, resin acid esters, polyoxyalkylene resin acid esters, polyoxyalkylene alkyl ethers, polyoxyalkylene alkylphenyl ethers, alkyl(poly)glycosides, polyoxyalkylene alkyl(poly)glycosides or etc. An ether group-containing nonionic surfactant having no nitrogen atom and an ester group-containing nonionic surfactant may be preferably included.

Examples of anionic surfactants include those surfactants based on carboxylic acid, sulfonic acid, sulfates or phosphates, among which the surfactants based on carboxylic acid or phosphates are preferable.

Examples of carboxylic acid-based surfactants include, $C_{6-30}$ fatty acids or salts thereof, polybasic carboxylic acid salts, polyoxyalkylene alkyl ether carboxylic acid salts, polyoxyalkylene alkylamide ether carboxylic acid salts, rhodinic acid salts, dimer acid salts, polymer acid salts, and tall oil fatty acid salts.

Examples of the sulfonic acid-based surfactants include, alkylbenzenesulfonic acid salts, alkylsulfonic acid salts, alkylnaphthalenesulfonic acid salts, naphthalenesulfonic acid salts, diphenyl ether sulfonic acid salts, condensates of alkylnaphthalene sulfonic acid, and conensates of alkylnaphthalene sulfonic acid.

Examples of the sulfate-based surfactants include, alkyl sulfates, polyoxyalkylene alkyl sulfates, polyoxyalkylene alkyl phenyl ether sulfates, tristyrenated phenol sulfates, polyoxyalkylene distyrenated phenol sulfates, and alkyl polyglycoside sulfates.

Examples of the phosphate-base surfactants include, alkyl phosphates, alkyl phenyl phosphates, polyoxyalkylene alkyl phosphates, and polyoxyalkylene alkyl phenyl phosphates.

Examples of the salts include, metallic salts (Na, K, Ca, Mg, Zn, etc.), ammonium salts, alkanol amine salts, fatty amine salts.

Examples of amphoteric surfactants include those surfactants based on amino acid, betaine, imidazoline, and amine oxide.

Examples of amino-acid based surfactants include, acylamino acid salts, acylsarcosine acid salts, acryloylmethylaminopropionic acid salts, alkylaminopropionic acid salts, and acylamide ethylhydroxyethylmethylcarboxylic acid salts.

Examples of betaine-based surfactants include alkyldimethylbetaine, alkylhydroxyethylbetaine, acylamide propylhydroxypropylammonia sulfobetaine, acylamide propylhydroxypropylammonia sulfobetaine, and ricinoleic acid amide propyl dimethylcarboxymethylammonia betaine.

Examples of imidazoline-based surfactants include alkylcarboxy methylhydroxy ethylimidazolinium betaine, and alkylethoxy carboxy methylimidazolium betaine.

Examples of amine oxide-based surfactants include alkyldimethylamine oxide, alkyldiethanolamine oxide, and alkylamidepropylamine oxide.

The surfactants described above may be used alone or as a mixture thereof. When these surfactants contain polyoxyalkylene groups, they preferably have polyoxyethylene groups, and the average number of molecules added thereto is 1 to 50.

The surfactant is preferably a nonionic surfactant, an amphoteric surfactant or an anionic surfactant, particularly preferably a nonionic surfactant. Specifically, the surfactant is preferably at least one selected from an ester group-containing nonionic surfactant, an ether group-containing nonionic surfactant having no nitrogen atom, an amphoteric surfactant, a carboxylic acid-based anionic surfactant and a phosphoric acid-based nonionic surfactant. The surfactant is particularly preferably at least one selected from an ester group-containing nonionic surfactant, an ether group-containing nonionic surfactant having no nitrogen atom and an ester group-containing nonionic surfactant.

Further, the following fertilizer components may be used in combination with the mono-alcohol described above. Specific examples thereof may be inorganic or organic components which can supply elements such as N, P, K, Ca, Mg, S, B, Fe, Mn, Cu, Zn, Mo, Cl, Si or Na, in particular N, P, K, Ca or Mg. Examples of such inorganic compounds include ammonium nitrate, potassium nitrate, ammonium sulfate, ammonium chloride, ammonium phosphate, sodium nitrate, urea, ammonium carbonate, potassium phosphate, calcium superphosphate, fused phosphate fertilizer ($3MgO \cdot CaO \cdot P_2O_5 \cdot 3CaSiO_2$), potassium sulfate, potassium chloride, nitrate of lime, slaked lime, carbonate of lime, magnesium sulfate, magnesium hydroxide, magnesium carbonate. Examples of the organic compounds include fowl droppings, cow dung, Bark compost, amino acids, peptone, amino acid solution, which is called Mieki in Japan, fermentation extracts, calcium salts of organic acids, such as citric acid, gluconic acid or succinic acid, and calcium salts of fatty acids, such as formic acid, acetic acid, propionic acid, caprylic acid, capric acid or caproic acid. These fertilizer components may be used in combination with the surfactant. In the case that fertilizer components are sufficiently applied as basal fertilizer to soil as seen in outdoor cultivation of a rice-plant or vegetables, it is unnecessary to mix the fertilizer components. Further, when a cultivation form is such as a fertigation (a hydroponic soil culture) or a hydroponics, when it avoids applying excessively basal fertilizer and when it is a type of providing a fertilizer component as well as irrigation-water, the fertilizer component is preferably mixed.

The plant-activating agent of this invention when mixed with a chelating agent, specifically the following organic acid having a chelating ability or a salt thereof attains further improvements in growth and the efficiency of absorption of fertilizers. The organic acid is specifically oxycarboxylic acids such as citric acid, gluconic acid, malic acid, heptonic acid, oxalic acid, malonic acid, lactic acid, tartaric acid, succinic acid, fumaric acid, maleic acid, adipic acid and glutaric acid; polybasic carboxylic acids; and salts thereof such as potassium salt, sodium salt, alkanolamine salt, aliphatic amine salt.

Further, the plant-activating agent of this invention when mixed with a chelating agent other than organic acids attains improvements in growth and the efficiency of absorption of fertilizers. Examples of the mixed chelating agents include aminocarboxylic acid-based chelating agents such as EDTA, NTA, and CDTA.

A thickener can be used in combination with the plant-activating agent of this invention. As the thickener, any of natural, semi-synthetic and synthetic water-soluble thickeners can be used, and specifically the natural thickeners include microorganism-derived xanthane gum and zanflow, plant-derived pectin, Arabia gum and guar gum and animal-derived gelatin and casein; the semi-synthetic thickeners include cellulose or starch-derived methylated or carboxyalkylated or hydroxyalkylated products (including methyl cellulose, carboxymethyl cellulose, hydroxymethyl cellulose, etc.), sorbitol, alginic acid derivatives (including propylene glycol alginic acid ester, alginic acid salts, etc.), and other polysaccharide derivatives (including stearyl sulfopolysaccharides etc.); and the synthetic thickeners include polyacrylates (including carboxyvinyl polymers etc.), polymaleate, polyvinyl pyrrolidone, pentaerythritol ethylene oxide adducts, ethylene oxide polymers, and ethylene oxide-propylene oxide block copolymers. In particular, the thickener is used preferably in the presence of a surfactant.

In the plant-activating agent of this invention, the respective components are compounded preferably in the following ratio to 100 parts by weight of the components (A) and (B) in total: the surfactant in an amount of 10 to 20000 parts by weight, particularly 100 to 2000 parts by weight; the fertilizer component, 0 to 50000 parts by weight, particularly 10 to 5000 parts by weight; the chelating agent, 0 to 1000 parts by weight, particularly 10 to 500 parts by weight; the thickener, 10 to 20000 parts by weight, particularly 10 to 2000 parts by weight; and other nutrient sources (sugars, amino acids, vitamins, etc.), 0 to 5000 parts by weight, particularly-10 to 500 parts by weight.

In the case that the plant-activating composition is applied in the form of a dust formulation or granule as fertilizer to soil, it is preferable that the used dust formulation or granule comprise the above-mentioned components except water at the same ratios as above, in general. This dust formulation or granule may comprise a vehicle to prevent caking.

The plant-activating agent of this invention can be formed into a liquid preparation which is stable in long-term storage, particularly in long-term storage under severe conditions such as high temperatures. The plant-activating agent of this invention when used in treatment at a suitable concentration can improve the activity of a plant effectively without chemical damage, and can thus be used in a wide variety of agricultural products. According to this invention, there can also be brought about improvements in plant growth such as promotion of taking roots of plant, an increase of chlorophyll value(SPAD value), and increase of absorption efficiency of fertilizers.

EXAMPLE

Example 1

Plant-activating agents (balance: water) with the compositions shown in Tables 1 to 3 were prepared and then evaluated for their storage stability and their effect of activating plants in the following manner.

As the components (A) and (B) in Tables 1 to 3, for example, $C_{18}$ alcohol means a saturated linear mono-alcohol containing 18 carbon atoms; this also applies to other alcohols.

As the component (C), POE is an abbreviation of polyoxyethylene, and the number in brackets shows the average number of added ethylene oxide. The fertilizer component is a mixture of 41.5 weight-% of urea, 31.5 weight-% of potassium nitrate, 22.8 weight-% of monopotassium hydrogen phosphate and 4.2 weight-% of dipotassium hydrogen phosphate. The carboxyvinyl polymer is Carbopole 981 (manufactured by Nikko Chemicals Co., Ltd.). Further, the stearyl sulfopolysaccharide, that is, the one wherein stearylglycidyl ether and sodium 2,3-epoxypropanesulfonate were added to hydroxyethyl cellulose (Natrozol 250 HHX manufactured by Hercules) as starting material such that the degree of substitution of 3-stearyloxy-2-hydroxypropyl group was 0.0037 and the degree of substitution of 3-sulfo-2-hydroxypropyl group was 0.115, was obtained according to a method in Example 1 in Japanese Patent Application No. 2001-114047.

(1) Storage Stability

The plant-activating agent was stored for 30 days at 50° C., 40° C. or room temperature (15 to 20° C.) and then observed for its appearance, and a one-phase and uniform state was evaluated as "⊙", a one-phase solution not separated into two (i.e. oil and aqueous) phases but showing a difference in density between an upper and lower parts was evaluated as "○", and a solution separated into two (i.e. oil and aqueous) phases was evaluated as "x".

(2) Effect of Activating Plants (2-1) Tomato Test (Tables 1 and 2)

Tomato seeds "Momotaro" were sowed, and the soil used was Kureha Engei Baido(horticultural soil made by Kureha Chemical Industry Co., Ltd.) (fertilizer component; N:P:K= 0.4:1.9:0.6 (g)/1 kg soil). After two leaves were developed, each seedling was planted in a pot of 15 cm in diameter, and treatment was initiated. The treatment with irrigation was carried out four times in total at seven-days intervals by treating one plant with 100 ml of a 150-fold dilution of a plant-activating agent shown in Tables 1 and 2. The treatment by spraying onto leaves was carried out in an analogous manner by treating one plant with 50 ml dilution. Seven days after treated 4 times, the weight of the whole of the plant was measured. The measured weight was compared as a relative value to that (=100) of the control group. The results are shown in Tables 1 and 2.

(2-2) Pakchoi Test (Table 3)

Pakchoi seeds were sowed, and the soil used was Kureha Engei Baido (horticultural soil made by Kureha Chemical Industry Co., Ltd.) (fertilizer component; N:P:K=0.4:1.9:0.6 (g)/1 kg soil). After two leaves were developed, each seedling was planted in a pot of 15 cm in diameter, and treatment was initiated. The treatment with irrigation was carried out five times in total at seven-days intervals by treating one plant with 100 ml of a 150-fold dilution of a plant-activating agent shown in Table 3. The treatment by spraying onto leaves was carried out in an analogous manner by treating one plant with 50 ml dilution. Six days after treated five times, the weight of the whole of the plant was measured. The measured weight was compared as relative value to that (=100) of the control group. The results are shown in Table 3.

TABLE 1

| No. | | Blended materials | Concentration (weight-%) | Storage stability 50° C. | 40° C. | Room temperatur | Activating effect (tomato) Irrigation | Spraying onto leaves |
|---|---|---|---|---|---|---|---|---|
| Invention product | 1 (A) | $C_{18}$ alcohol | 0.60 | ◎ | ◎ | ◎ | 123 | 111 |
| | (B) | $C_{24}$ alcohol | 0.24 | | | | | |
| | (C) | POE(60) hardened castor oil | 1.20 | | | | | |
| | | Fertilizer component | 2.50 | | | | | |
| | 2 (A) | $C_{18}$ alcohol | 0.60 | ◎ | ◎ | ◎ | 127 | 114 |
| | (B) | $C_{24}$ alcohol | 0.24 | | | | | |
| | (C) | POE(60) hardened castor oil | 1.20 | | | | | |
| | | Na gluconate | 0.10 | | | | | |
| | | Fertilizer component | 2.50 | | | | | |
| | 3 (A) | $C_{16}$ alcohol | 0.80 | ○ | ◎ | ◎ | 120 | 110 |
| | (B) | $C_{28}$ alcohol | 0.20 | | | | | |
| | (C) | POE(60) hardened castor oil | 2.50 | | | | | |
| | | Fertilizer component | 5.00 | | | | | |
| | 4 (A) | $C_{18}$ alcohol | 0.60 | ◎ | ◎ | ◎ | 122 | 112 |
| | (B) | $C_{22}$ alcohol | 0.36 | | | | | |
| | (C) | POE(80) hardened castor oil | 1.80 | | | | | |
| | | Fertilizer component | 2.90 | | | | | |
| | 5 (A) | $C_{18}$ alcohol | 0.60 | ◎ | ◎ | ◎ | 128 | 115 |
| | (B) | $C_{22}$ alcohol | 0.36 | | | | | |
| | (C) | POE(80) hardened castor oil | 1.80 | | | | | |
| | | 3Na citrate | 0.24 | | | | | |
| | | Fertilizer component | 2.90 | | | | | |
| | 6 (A) | $C_{18}$ alcohol | 0.60 | ◎ | ◎ | ◎ | 126 | 114 |
| | (B) | $C_{22}$ alcohol | 0.36 | | | | | |
| | (C) | POE(80) hardened castor oil | 1.80 | | | | | |
| | | 3Na citrate | 0.24 | | | | | |
| | | Fertilizer component | 2.90 | | | | | |
| | | Carboxyvinyl polymer | 0.15 | | | | | |
| | 7 (A) | $C_{18}$ alcohol | 0.60 | ◎ | ◎ | ◎ | 125 | 114 |
| | (B) | $C_{22}$ alcohol | 0.25 | | | | | |
| | (C) | POE(80) hardened castor oil | 1.50 | | | | | |
| | | 3Na citrate | 0.20 | | | | | |
| | | Fertilizer component | 2.90 | | | | | |
| | | Stearyl sulfopolysaccharide | 0.10 | | | | | |
| Control: fertilizer component | | | 3.00 | — | — | — | 100 | 100 |

TABLE 2

| No. | | Blended raw | Concentration (weight-%) | Storage stability 50° C. | 40° C. | Room temperature | Activating effect (tomato) Irrigation | Spraying onto leaves |
|---|---|---|---|---|---|---|---|---|
| Invention | 8 (A) | $C_{14}$ alcohol | 0.50 | ○ | ◎ | ◎ | 117 | 108 |
| | (B) | $C_{26}$ alcohol | 0.30 | | | | | |

TABLE 2-continued

|   |   | No. |   | Blended raw | Concentration (weight-%) | Storage stability 50° C. | 40° C. | Room temperature | Activating effect (tomato) Irrigation | Spraying onto leaves |
|---|---|---|---|---|---|---|---|---|---|---|
| prod- uct |   |   | (C) | POE(100) hardened castor oil | 2.00 |   |   |   |   |   |
|   |   |   |   | Fertilizer component | 4.50 |   |   |   |   |   |
|   |   | 9 | (A) | C$_{18}$ alcohol | 0.60 | ○ | ◉ | ◉ | 125 | 114 |
|   |   |   | (B) | C$_{22}$ alcohol | 0.24 |   |   |   |   |   |
|   |   |   | (C) | POE(20) sorbitan monostearate | 0.90 |   |   |   |   |   |
|   |   |   |   | Sorbitan monostearate | 0.90 |   |   |   |   |   |
|   |   |   |   | 3Na citrate | 0.25 |   |   |   |   |   |
|   |   |   |   | Fertilizer component | 3.00 |   |   |   |   |   |
|   |   | 10 | (A) | C$_{18}$ alcohol | 0.60 | ○ | ◉ | ◉ | 124 | 114 |
|   |   |   | (B) | C$_{22}$ alcohol | 0.35 |   |   |   |   |   |
|   |   |   | (C) | POE(20) sorbitan monooleate | 0.90 |   |   |   |   |   |
|   |   |   |   | Sorbitan monooleate | 0.90 |   |   |   |   |   |
|   |   |   |   | EDTA4Na | 0.25 |   |   |   |   |   |
|   |   |   |   | Fertilizer component | 3.00 |   |   |   |   |   |
|   |   | 11 | (A) | C$_{18}$ alcohol | 0.60 | ◉ | ◉ | ◉ | 123 | 114 |
|   |   |   | (B) | C$_{22}$ alcohol | 0.36 |   |   |   |   |   |
|   |   |   | (C) | POE(20) sorbitan monostearate | 0.22 |   |   |   |   |   |
|   |   |   |   | Sorbitan monostearate | 0.22 |   |   |   |   |   |
|   |   |   |   | POE(80) hardened castor oil | 1.35 |   |   |   |   |   |
|   |   |   |   | 3Na citrate | 0.25 |   |   |   |   |   |
|   |   |   |   | Fertilizer component | 3.00 |   |   |   |   |   |
| Compara- tive prod- uct |   | 1 | (A) | C$_{12}$ alcohol | 0.60 | X | X | X | 112 | 107 |
|   |   |   | (C) | POE(9) nonyl phenyl ether | 1.20 |   |   |   |   |   |
|   |   |   |   | Fertilizer component | 2.50 |   |   |   |   |   |
|   |   | 2 | (A) | C$_{14}$ alcohol | 0.60 | X | X | X | 116 | 108 |
|   |   |   | (C) | POE(9) nonyl phenyl ether | 1.20 |   |   |   |   |   |
|   |   |   |   | Fertilizer component | 3.00 |   |   |   |   |   |
|   |   | 3 | (A) | C$_{12}$ alcohol | 0.60 | X | X | X | 115 | 107 |
|   |   |   |   | C$_{14}$ alcohol | 0.45 |   |   |   |   |   |
|   |   |   | (C) | POE(9) nonyl phenyl ether | 1.80 |   |   |   |   |   |
|   |   |   |   | Fertilizer component | 2.90 |   |   |   |   |   |
| Control: fertilizer component |   |   |   |   | 3.00 | — | — | — | 100 | 100 |

TABLE 3

|   |   | No. |   | Blended raw | Concentration (weight-%) | Storage stability 50° C. | 40° C. | Room temperature | Activating effect (Pakchoi) Irrigation | Spraying onto leaves |
|---|---|---|---|---|---|---|---|---|---|---|
| Inven- tion prod- uct |   | 12 | (A) | C$_{16}$ alcohol | 0.80 | ○ | ◉ | ◉ | 125 | 111 |
|   |   |   | (B) | C$_{24}$ alcohol | 0.15 |   |   |   |   |   |
|   |   |   | (C) | POE(60) hardened castor oil | 2.50 |   |   |   |   |   |
|   |   | 13 | (A) | C$_{18}$ alcohol | 0.60 | ◉ | ◉ | ◉ | 130 | 114 |
|   |   |   | (B) | C$_{22}$ alcohol | 0.36 |   |   |   |   |   |
|   |   |   | (C) | POE(80) hardened caster oil | 1.80 |   |   |   |   |   |
|   |   | 14 | (A) | C$_{18}$ alcohol | 0.60 | ◉ | ◉ | ◉ | 135 | 119 |
|   |   |   | (B) | C$_{22}$ alcohol | 0.36 |   |   |   |   |   |
|   |   |   | (C) | POE(80) hardened caster oil | 1.80 |   |   |   |   |   |
|   |   |   |   | 3Na citrate | 0.24 |   |   |   |   |   |
|   |   | 15 | (A) | C$_{18}$ alcohol | 0.60 | ◉ | ◉ | ◉ | 134 | 119 |
|   |   |   | (B) | C$_{22}$ alcohol | 0.36 |   |   |   |   |   |
|   |   |   | (C) | POE(80) hardened caster oil | 1.80 |   |   |   |   |   |
|   |   |   |   | 3Na citrate | 0.24 |   |   |   |   |   |
|   |   |   |   | Carboxyvinyl polymer | 0.15 |   |   |   |   |   |
|   |   | 16 | (A) | C$_{16}$ alcohol | 0.60 | ○ | ◉ | ◉ | 124 | 111 |
|   |   |   | (B) | C$_{24}$ alcohol | 0.24 |   |   |   |   |   |
|   |   |   | (C) | POE(20) sorbitan monostearate | 0.90 |   |   |   |   |   |
|   |   |   |   | Sorbitan monostearate | 0.90 |   |   |   |   |   |
|   |   |   |   | 3Na citrate | 0.25 |   |   |   |   |   |
|   |   | 17 | (A) | C$_{16}$ alcohol | 0.60 | ○ | ◉ | ◉ | 123 | 110 |
|   |   |   | (B) | C$_{24}$ alcohol | 0.36 |   |   |   |   |   |
|   |   |   | (C) | POE(20) Sorbita monostearate | 0.22 |   |   |   |   |   |
|   |   |   |   | Sorbitan monostearate | 0.22 |   |   |   |   |   |

TABLE 3-continued

| No. | | | Blended raw | Concentration (weight-%) | Storage stability 50° C. | 40° C. | Room temperature | Activating effect (Pakchoi) Irrigation | Spraying onto leaves |
|---|---|---|---|---|---|---|---|---|---|
| | | | POE(80) hardened castor oil | 1.35 | | | | | |
| | | | 3Na citrate | 0.25 | | | | | |
| Comparative product | 4 | (A) | $C_{12}$ alcohol | 0.60 | X | X | X | 109 | 107 |
| | | (C) | POE(9) nonyl phenyl ether | 1.20 | | | | | |
| | 5 | (A) | $C_{14}$ alcohol | 0.60 | X | X | X | 112 | 108 |
| | | (C) | POE(9) nonyl phenyl ether | 1.20 | | | | | |
| | 6 | (A) | $C_{12}$ alcohol | 0.60 | X | X | X | 113 | 107 |
| | | | $C_{14}$ alcohol | 0.45 | | | | | |
| | | (C) | POE(9) nonyl phenyl ether | 1.80 | | | | | |
| Control: Water | | | | — | — | — | — | 100 | 100 |

Example 2

The average particle diameter of solid particles in each the invented plant-activating agents Nos. 1, 3, 4, 5, 6 and 9 in Example 1 was measured at an initial production stage and after storage. In the storage, the plant-activating agents were left for 30 days at 40° C. or room temperature (15 to 20° C.), and then the average particle diameter of solid particles in each of the plant-activating agents was measured. For measurement of the average particle diameter, a laser diffraction/scattering particle size distribution-measuring meter (LA-700 manufactured by Horiba, Ltd.) was used. The results are shown in Table 4.

What is claimed is:

1. A plant-activating agent composition comprising (A) a $C_{12-19}$ mono-alcohol and (B) a $C_{20-30}$ mono-alcohol.

2. A plant-activating agent composition comprising (A) a $C_{12-19}$ mono-alcohol, (B) a $C_{20-30}$ mono-alcohol, and (C) at least one selected from the group consisting of a surfactant, a fertilizer component and a chelating agent.

3. The plant-activating agent composition according to claim 1 or 2, wherein the ratio by weight of (A) the $C_{12-19}$ mono-alcohol to (B) the $C_{20-30}$ mono-alcohol, that is, (A)/(B), is 20/1 to 1/20.

4. The plant-activating agent composition according to claim 1 or 2, which further comprises a thickener.

TABLE 4

| No. | | | Blended raw | Concentration (weight-%) | At an initial production stage | After storage at 40° C. for 30 days | After storage at room temperature for 30 days |
|---|---|---|---|---|---|---|---|
| Invention product | 1 | (A) | $C_{18}$ alcohol | 0.60 | 0.56 | 0.83 | 3.21 |
| | | (B) | $C_{24}$ alcohol | 0.24 | | | |
| | | (C) | POE(60) hardened caster oil | 1.20 | | | |
| | | | Fertilizer component | 2.50 | | | |
| | 3 | (A) | $C_{16}$ alcohol | 0.80 | 1.24 | 1.87 | 10.21 |
| | | (B) | $C_{28}$ alcohol | 0.20 | | | |
| | | (C) | POE(60) hardened caster oil | 2.50 | | | |
| | | | Fertilizer component | 5.00 | | | |
| | 4 | (A) | $C_{18}$ alcohol | 0.60 | 0.25 | 0.38 | 4.69 |
| | | (B) | $C_{22}$ alcohol | 0.36 | | | |
| | | (C) | POE(80) hardened castor oil | 1.80 | | | |
| | | | Fertilizer component | 2.90 | | | |
| | 5 | (A) | $C_{18}$ alcohol | 0.60 | 0.30 | 0.42 | 5.23 |
| | | (B) | $C_{22}$ alcohol | 0.36 | | | |
| | | (C) | POE(80) hardened castor oil | 1.80 | | | |
| | | | 3Na citrate | 0.24 | | | |
| | | | Fertilizer component | 2.90 | | | |
| | 6 | (A) | $C_{18}$ alcohol | 0.60 | 2.42 | 3.82 | 4.28 |
| | | (B) | $C_{22}$ alcohol | 0.36 | | | |
| | | (C) | POE(80) hardened castor oil | 1.80 | | | |
| | | | 3Na citrate | 0.24 | | | |
| | | | Fertilizer component | 2.90 | | | |
| | | | Carboxyvinyl polymer | 0.15 | | | |
| | 9 | (A) | $C_{18}$ alcohol | 0.60 | 12.04 | 15.02 | 16.21 |
| | | (B) | $C_{22}$ alcohol | 0.24 | | | |
| | | (C) | POE(20) sorbitan monostearate | 0.90 | | | |
| | | | Sorbitan monostearate | 0.90 | | | |
| | | | 3Na citrate | 0.25 | | | |
| | | | Fertilizer component | 3.00 | | | |

5. A plant-activating agent composition comprising particles having an average particle diameter of 0.01 to 500 μm, and comprising at least one selected from the group consisting of (A) a $C_{12-19}$ mono-alcohol and (B) a $C_{20-30}$ mono-alcohol.

6. The plant-activating agent composition according to claim 5, which further comprises (C) at least one selected from the group consisting of a surfactant, a fertilizer component and a chelating agent.

7. The plant-activating agent composition according to claim 5 or 6, which comprises (A) the $C_{12-19}$ mono-alcohol to (B) the $C_{20-30}$ mono-alcohol wherein the ratio of (A)/(B) by weight is 20/1 to 1/20.

8. A method of improving the activity of a plant, which comprises supplying the plant-activating agent composition of claim 1 or 2 to the plant.

9. A method of improving the activity of a plant, which comprises supplying the plant-activating agent composition of claim 5 to the plant.

10. The method according to claim 9, wherein the composition further comprises at least one selected from the group consisting of (C) a surfactant, a fertilizer component and a chelating agent.

11. A plant-activating agent composition comprising (A) a $C_{12-19}$ mono-alcohol, (B) a $C_{20-30}$ mono-alcohol, (C') a nonionic surfactant and at least one selected from the group consisting of a fertilizer component and a chelating agent.

* * * * *